United States Patent
Hafner

(10) Patent No.: US 9,610,827 B2
(45) Date of Patent: Apr. 4, 2017

(54) CONNECTING ADAPTER FOR CONNECTING FRAGRANCE CONTAINER TO FRAGRANCE EMITTER AND FRAGRANCE APPARATUS WITH SUCH CONNECTING ADAPTER

(71) Applicant: Leopold Kostal GmbH & Co. KG, Luedenscheid (DE)

(72) Inventor: Tobias Hafner, Dortmund (DE)

(73) Assignee: Leopold Kostal GmbH & Co. KG, Luedenscheid (DE)

(*) Notice: Subject to any disclaimer, the term of this patent is extended or adjusted under 35 U.S.C. 154(b) by 0 days.

(21) Appl. No.: 14/967,484

(22) Filed: Dec. 14, 2015

(65) Prior Publication Data

US 2016/0096415 A1    Apr. 7, 2016

Related U.S. Application Data

(63) Continuation of application No. PCT/EP2014/065295, filed on Jul. 16, 2014.

(30) Foreign Application Priority Data

Jul. 19, 2013  (DE) .................. 10 2013 012 021

(51) Int. Cl.
*A62C 13/62*  (2006.01)
*B60H 3/00*  (2006.01)
*A61L 9/12*  (2006.01)

(52) U.S. Cl.
CPC .............. *B60H 3/0035* (2013.01); *A61L 9/12* (2013.01); *B60H 3/0021* (2013.01); *B60H 2003/005* (2013.01); *B60H 2003/0057* (2013.01)

(58) Field of Classification Search
CPC ................ B60H 3/0035; B60H 3/0021; B60H 2003/005; B60H 2003/0057; A61L 9/12
(Continued)

(56) References Cited

U.S. PATENT DOCUMENTS 5,697,534 A * 12/1997 Huyghe ................ B05B 15/065
                                                                  222/527
2007/0072448 A1  3/2007 Hoppe et al.
2013/0277456 A1  10/2013 Fehling

FOREIGN PATENT DOCUMENTS

CN    200960310 Y    10/2007
CN    202355614 U    8/2012
(Continued)

OTHER PUBLICATIONS

The International Bureau of WIPO, International Preliminary Report on Patentability for International Application No. PCT/EP2014/065295 issued Jan. 19, 2016.
(Continued)

*Primary Examiner* — Davis Hwu
(74) *Attorney, Agent, or Firm* — Brooks Kushman P.C.

(57) ABSTRACT

A fragrance apparatus for distributing fragrance in a vehicle includes a connecting adapter for connecting a fragrance container to a fragrance emitter device. The connecting adapter includes a fixed component, a movable component, and springs connected between the fixed component and the movable component. The movable component is pivotable with respect to the fixed component through the springs to compensate for any angular misalignment between the movable component and the fragrance container when the movable component is attached to the fragrance container.

19 Claims, 3 Drawing Sheets

(58) Field of Classification Search
USPC .......................................................... 239/302
See application file for complete search history.

(56) References Cited

FOREIGN PATENT DOCUMENTS

| | | |
|---|---|---|
| DE | 10344308 A1 | 4/2004 |
| DE | 102006028399 A1 | 1/2007 |
| DE | 102005046736 A1 | 5/2007 |
| DE | 102006023713 A1 | 11/2007 |
| DE | 102010008436 A1 | 8/2011 |
| DE | 102011010277 A1 | 8/2012 |

OTHER PUBLICATIONS

European Patent Office, International Search Report for corresponding International Application No. PCT/EP2014/065295 mailed Oct. 29, 2014.

The State Intellectual Property Office of People's Republic of China, Translation for the First Chinese Office Action for the corresponding Chinese Patent Application No. 201480034335.3, dated Sep. 14, 2016.

The State Intellectual Property Office of People's Republic of China, The First Search for the corresponding Chinese Patent Application No. 201480034335.3 dated Sep. 2, 2016.

* cited by examiner

CONNECTING ADAPTER FOR CONNECTING FRAGRANCE CONTAINER TO FRAGRANCE EMITTER AND FRAGRANCE APPARATUS WITH SUCH CONNECTING ADAPTER

CROSS-REFERENCE TO RELATED APPLICATIONS

This application is a continuation of International Application No. PCT/EP2014/065295, published in German, with an International filing date of Jul. 16, 2014, which claims priority to DE 10 2013 012 021.7, filed Jul. 19, 2013; the disclosures of which are hereby incorporated in their entirety by reference herein.

TECHNICAL FIELD

The present invention relates to a connecting adapter for connecting a fragrance container having a valve cap with a spring-loaded valve plate to a fragrance emitter device for emitting fragrance from the fragrance container in a vehicle, the connecting adapter being attached to the valve cap of the fragrance container to thereby open the valve plate and the connecting adapter connecting the fragrance container to the fragrance emitter device.

BACKGROUND

DE 10 2010 008 436 A1 describes a fragrance apparatus for emitting fragrance in a motor vehicle. The apparatus includes a fragrance container and an electrical fragrance emitter device. The fragrance container has a valve cap with a spring-loaded valve plate. The valve plate is displaced in an opened position when a connecting adapter is attached to a connecting surface of the valve cap. The fragrance container conducts a current with the electrical fragrance emitter device connected thereto via the connecting adapter to produce an air flow that meters the fragrance contained in the fragrance container. The fragrance emitter device distributes the metered fragrance into the interior of the vehicle. The connecting adapter is immovably fixed.

The valve plate is connected to a tubular part through the neck of the fragrance container, which forms a component of the valve mechanism. Because of this the valve plate can be displaced perpendicular to its main surface, but can tip only slightly. A tipping of the fragrance container against the immovably fixed connecting adapter can thereby be compensated by the valve plate only to a small extent.

It should be assured that the connection between the fragrance container and the fragrance emitter device is gas-tight. A gas-tight connection is desired so that the air current enriched with the fragrance is conducted to the target destination through the entire system and does not leak at undesired locations. Tolerances in height and angular errors may occur when different components such as the fragrance container and the fragrance emitter device are connected together because of their mutual play. The height tolerances and angular errors have to be compensated. Since the connecting surface of the valve cap of the fragrance container is a plane that can be tipped in various directions, the angular errors are not restricted to a single directional axis.

SUMMARY

An object is a connecting adapter which automatically compensates for angular misalignment at the connection junction between the connecting adapter and a fragrance container.

In carrying out at least one of the above and/or other objects, a connecting adapter for connecting a fragrance container to a fragrance emitter device for distributing fragrance is provided. The connecting adapter includes a fixed component, a movable component, and springs connected between the fixed component and the movable component. The movable component is pivotable with respect to the fixed component through the springs to compensate for any angular misalignment between the movable component and the fragrance container when the movable component is attached to the fragrance container.

The fixed component may include retaining elements. In this case, the movable component is mounted to the fixed component through the retaining elements. The springs may be connected between the fixed component and the movable component to press the movable component against end sections of the retaining elements, respectively.

The springs individually compress differently in response to different forces applied against different locations of the movable component toward the fixed component such that the movable component is pivotable about two directional axes in a plane.

The fixed component may include a central projection for engaging a valve tappet of the fragrance container. In this case, the springs are arranged symmetrically about the central projection.

Further, in carrying out at least one of the above and/or other objects, a fragrance apparatus for distributing fragrance in a vehicle is provided. The fragrance apparatus includes a fragrance container and a connecting adapter. The connecting adapter has a fixed component, a movable component, and springs connected between the fixed component and the movable component. The connecting adapter is connected to the fragrance container with the movable component being arranged against the fragrance container. The movable component is pivotable with respect to the fixed component through the springs to compensate for any angular misalignment between the connecting adapter and the fragrance container.

Also, in carrying out at least one of the above and/or other objects, another fragrance apparatus for distributing fragrance in a vehicle is provided. This fragrance apparatus includes a fragrance container having a valve cap including a connecting surface. The fragrance apparatus further includes a connecting adapter having a fixed component, a movable component, and springs connected between the fixed component and the movable component. The movable component is attached to the connecting surface of the valve cap of the fragrance container to connect the connecting adapter to the fragrance container. The movable component is pivotable with respect to the fixed component through the springs to compensate for any angular misalignment between the movable component and the connecting surface of the valve cap of the fragrance container.

An embodiment provides a connecting adapter for connecting a fragrance container to an electrical fragrance emitter device for emitting fragrance in a vehicle. The connecting adapter is arranged on the fragrance emitter device. The fragrance container has a valve cap with a spring-loaded valve plate. The connecting adapter is attached to the fragrance container by being attached to the valve cap of the fragrance container. The connecting adapter opens the valve plate while being attached to the valve cap. The connecting adapter connects the fragrance container to the fragrance emitter device as the connecting adapter is attached to the fragrance container and is arranged on the fragrance emitter device.

The connecting adapter has a first fixed component, a second movable component, and at least one spring connected between the fixed component and the movable component. The fixed component is arranged on the fragrance emitter device for the connecting adapter to be arranged on the fragrance emitter device. The fixed component is thereby fixed in relation to the fragrance emitter device. The movable component is arranged against the valve cap of the fragrance container while the connecting adapter is attached to the fragrance container. For instance, the movable component is connected to a connecting surface of the valve cap of the fragrance container for the connecting adapter to be attached to the valve cap. The movable component is movable against the fixed component counter to forces of the at least one spring.

Another embodiment provides a fragrance apparatus having the fragrance container and the connecting adapter. The movable component of the connecting adapter is arranged against the fragrance container while the connecting adapter is attached to a connecting surface of a valve cap of the fragrance container. The connecting adapter opens a valve plate of the valve cap of the fragrance container while the connecting adapter is attached to the connecting surface of the valve cap. The fixed component of the connecting adapter may be arranged on a fragrance emitter device to arrange the connecting adapter on the fragrance emitter device and thereby connect the fragrance emitter device to the fragrance container through the connecting adapter. The movable component is movable against the fixed component to compensate for angular misalignment at the connection junction between the connecting adapter and the fragrance container.

In embodiments, a connecting adapter for connecting a fragrance container to a fragrance emitter device includes a first fixed component, a second movable component, and at least one helical spring connected between the fixed component and the movable component. The fixed component is attachable to the fragrance emitter device and is stationary with respect to the fragrance emitter device when attached thereto. The movable component can be pivoted or swiveled relative to the fixed component against the force of the at least one spring. The movable component is attachable to the fragrance container.

In embodiments, the connecting adapter has a first fixed component and a second movable component that can swivel about the vertical axis. Both components are connected to one another by at least one tolerance-compensating elastic or spring element, for example by one or more helical springs.

DETAILED DESCRIPTION

Detailed embodiments of the present invention are disclosed herein; however, it is to be understood that the disclosed embodiments are merely exemplary of the invention that may be embodied in various and alternative forms. The figures are not necessarily to scale; some features may be exaggerated or minimized to show details of particular components. Therefore, specific structural and functional details disclosed herein are not to be interpreted as limiting, but merely as a representative basis for teaching one skilled in the art to variously employ the present invention.

Initially, referring to FIGS. 3a and 3b, a problem will be briefly described with the aid of FIG. 3a and a suggested solution principle to the problem will be described briefly with the aid of FIG. 3b. In this regard, FIG. 3a illustrates a sketched representation of a conventional, immovably mounted connecting adapter 3 attached to a fragrance container 1 whereas FIG. 3b illustrates a sketched representation of a movably mounted connecting adapter 3 in accordance with embodiments of the present invention attached to fragrance container 1.

Figure 3A:
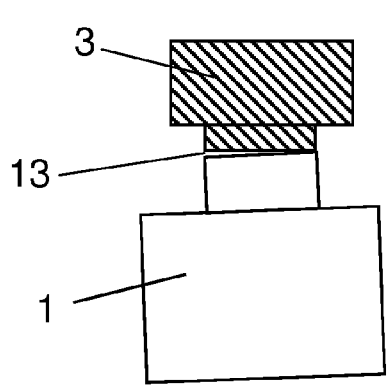
FIG. 3a illustrates a sketched representation of a conventional, immovably mounted connecting adapter attached to a fragrance container.
Figure 3B:
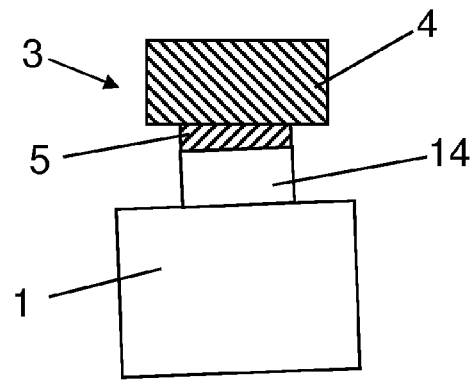
FIG. 3b illustrates a sketched representation of a movably mounted connecting adapter in accordance with embodiments of the present invention attached to a fragrance container.

In each of FIGS. 3a and 3b, connecting adapter 3 is connected to a neck 14 of fragrance container 1. Connecting adapter 3 may be a component of an electrical fragrance emitter device (not shown). Reference is made to DE 10 2010 008 436 A1 for a description in detail of the design and functionality of the fragrance emitter device. In principle, the function of the fragrance emitter device is to produce an air flow which promotes vaporized fragrance from fragrance container 1 and transports the vaporized fragrance to specific points in a vehicle through tube or hose connections.

Fragrance container 1 is not an integral component of the fragrance emitter device. Instead, fragrance container 1 is to be appended or connected to the fragrance emitter device and is to be able to be readily separated from the fragrance emitter device. Therefore, connecting adapter 3 is provided. Connecting adapter 3 is arranged on the fragrance emitter device and is attachable to fragrance container 1 to thereby connect fragrance container 1 to the fragrance emitter device. Connecting adapter 3 connected between fragrance container 1 and the fragrance emitter device connects the interior space of fragrance container 1 by a streaming flow with the fragrance emitter device. Here it must be assured that the connection between fragrance container 1 and connecting adapter 3 is gas-tight so that no vapors of the fragrance leak at the point of the connection.

No positive connection such as a screw connection is intentionally implemented between fragrance container 1 and connecting adapter 3. As such, a problem with achieving an especially simple connection and disconnection is that an imprecise force-fit connection between fragrance container 1 and connecting adapter 3 can rapidly lead to fragrance leakage. For example, as shown in FIG. 3a, when fragrance container 1 is only slightly tilted against the immovably mounted connecting adapter 3, an intermediate space 13 results at the point of connection between connecting adapter 3 and fragrance container 1 from which vaporized fragrance can escape.

With reference to FIG. 3b, the solution to this problem includes connecting adapter 3 having a first fixed component 4 and a second movable component 5. Fixed component 4 is to be arranged on the fragrance emitter device. Fixed component 4 is fixed with respect to the fragrance emitter device when the fixed component is arranged on the fragrance emitter device. Movable component 5 is arranged to tilt or pivot with respect to fixed component 4. The tilting or pivoting of movable component 4 with respect to fixed component 4 compensates for position tolerances of fragrance container 1. Accordingly, as is shown in FIG. 3b, movable component 5 is tilted with respect to fixed component 4 and thereby lies flat on the upper side of neck 14 of fragrance container 1. Consequently, any intermediate space 13 between connecting adapter 3 and fragrance container 1, which is present with the immovably mounted connecting adapter as is shown in FIG. 3a, is eliminated.

Figure 1:
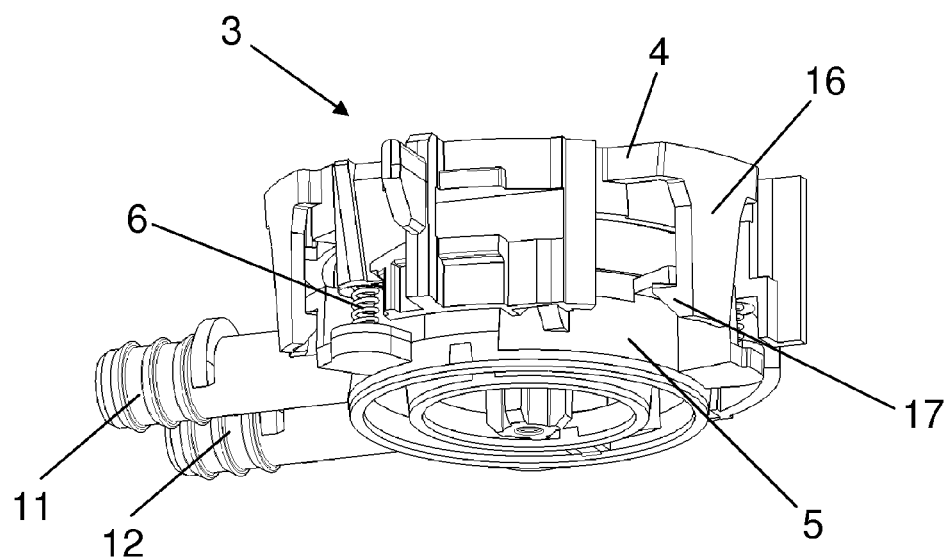
FIG. 1 illustrates a plan view of a connecting adapter in accordance with an embodiment of the present invention for connecting a fragrance container to a fragrance emitter device.
Figure 2:
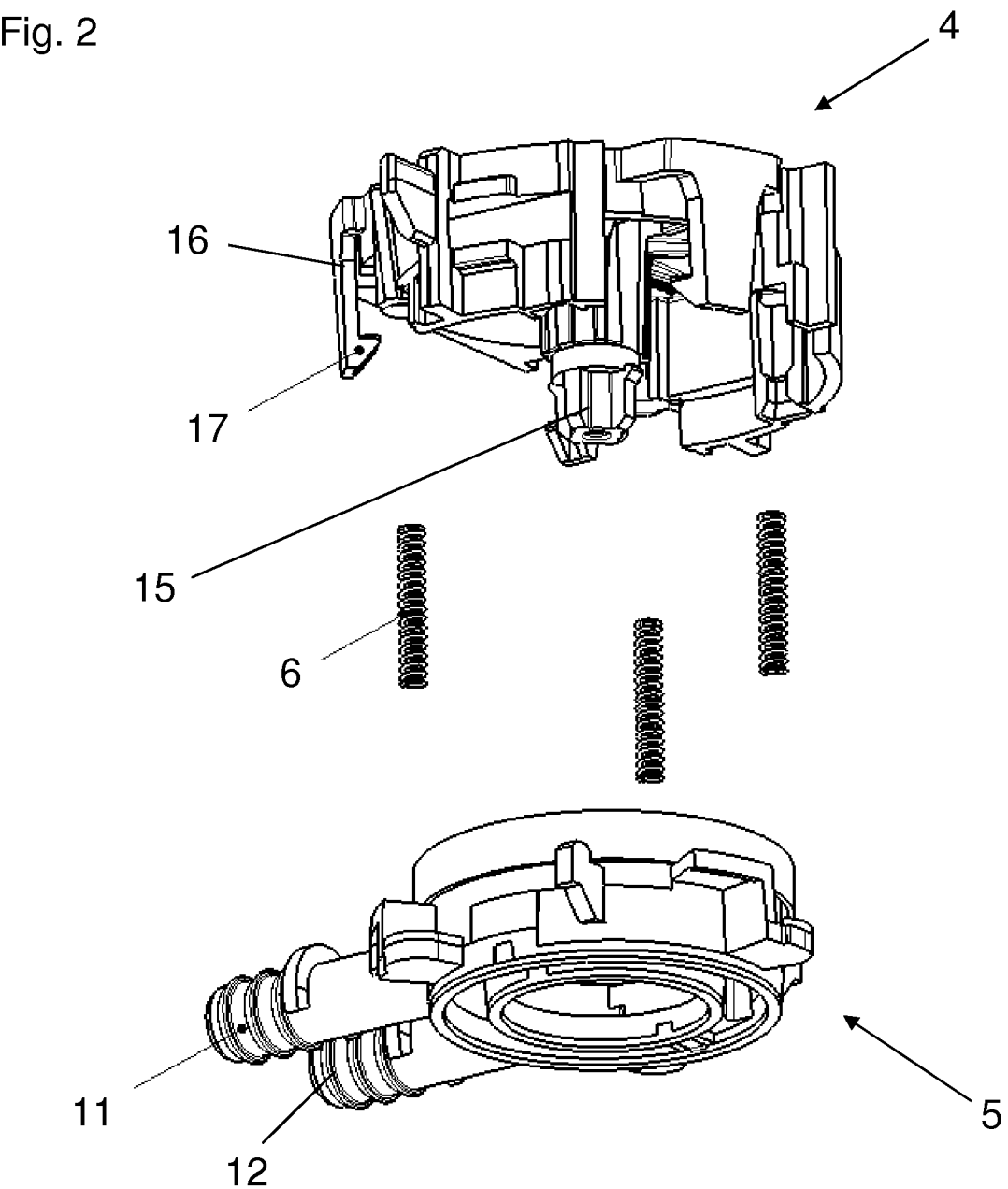
FIG. 2 illustrates an exploded view of the connecting adapter in accordance with the embodiment of the present invention.

Referring now to FIGS. 1 and 2, connecting adapter 3 in accordance with an embodiment of the present invention will be described. Connecting adapter 3 is for connecting a fragrance container 1 to a fragrance emitter device. Connecting adapter 3 includes first fixed component 4, second movable component 5, and a plurality of helical springs 6. Springs 6 extend between movable component 4 and fixed component 5 and connect movable component 5 to fixed component 4 at respective locations. In this way, movable component 5 is mounted to fixed component 4. The respective connections of springs 6 between fixed component 4 and movable component 5 enable movable component 5 to be able to tilt or pivot with respect to fixed component 4.

Fixed component 4 is to be fixedly arranged or mounted on the fragrance emitter device. Fixed component 4 includes a central pin-shaped axially extending projection 15 and a plurality of retaining elements 16. Three springs 6 are supported on movable component 5 and are arranged symmetrically about central projection 15. Movable component 5 is mounted on fixed component 4 through retaining elements 16 of fixed component 4. As is shown in FIG. 1, springs 6 press the housing of movable component 5 against bearing surfaces of hook-shaped end sections 17 of retaining elements 16.

Each spring 6 can be compressed by forces acting on the bottom end of the spring, which presses against movable component 5. As such, springs 6 compress by forces acting from below against movable component 5. Consequently, movable component 5 can be pushed axially against fixed component 4 or can be also tipped about two directional axes in the horizontal plane. In this manner, arbitrary misalignments of fragrance container 1 with respect to connecting adapter 3 are compensated to thereby prevent an intermediate space between fragrance container 1 and connecting adapter 3 from which fragrance can escape.

Figure 4:
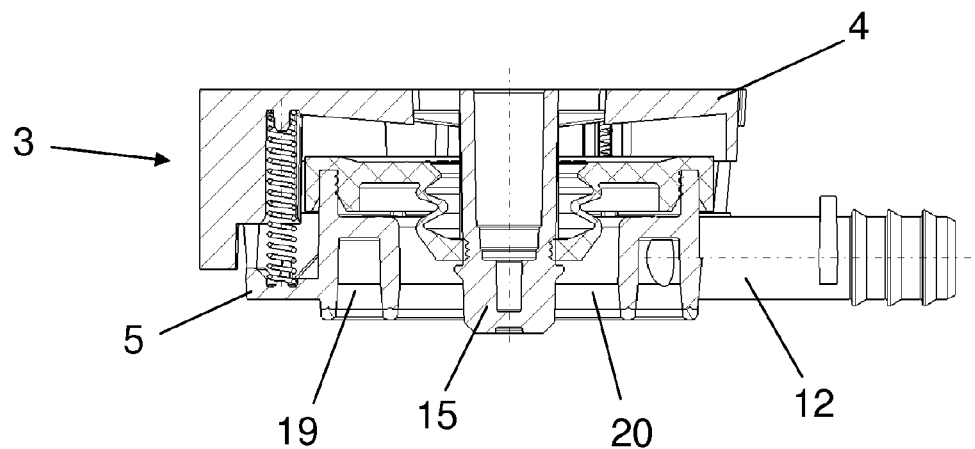
FIG. 4 illustrates a sectional view of the connecting adapter in accordance with the embodiment of the present invention.
Figure 5:
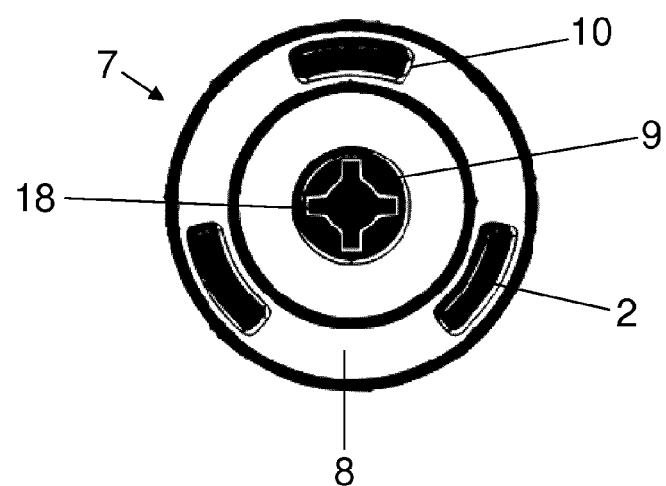
FIG. 5 illustrates a top view of a valve cap of the fragrance container which is to be connected to the fragrance emitter device through the connecting adapter in accordance with the embodiment of the present invention.

Referring now to FIGS. 4 and 5, with continual reference to FIGS. 1 and 2, the connection of connecting adapter 3 to fragrance container 1 will be described. The connection provides a flow-conducting or streaming flow connection between connecting adapter 3 and the interior of fragrance container 1.

As shown in FIG. 5, fragrance container 1 includes a valve cap 7. Valve cap 7 is screwed onto the top of fragrance container 1. A connecting surface 8 of fragrance container 1 is on the upper side of valve cap 7. Valve cap 7 has a central valve opening 9 and a plurality of annular shaped valve openings 10. A valve plate 2 is spring-loaded inside valve cap 7. Valve plate 2 closes off valve openings 9 and 10. The sections of valve plate 2 that close valve openings 9 and 10 are shown by dark areas in FIG. 5. A valve tappet 18 is connected to valve plate 2. Valve plate 2 may be pushed against the force of a valve spring (not shown) located inside valve cap 7 whereby valve openings 9 and 10 are released by pressure activation of valve tappet 18.

This pressure activation is achieved by appending connecting adapter 3 to fragrance container 1. In particular, central projection 15 of connecting adapter 3 engages valve tappet 18 when connecting adapter 3 is connected to fragrance container 1. In the connection process, central projection 15 extends into central valve opening 9, which simultaneously assures that connecting surface 8 of fragrance container 1 is sufficiently well centered below connecting adapter 3. In this manner, annular-shaped valve openings 10 are located precisely below ring gaps 19 of connecting adapter 3 (shown in FIG. 4). Ring gaps 19 are connected by a streaming flow with an input channel 11 (shown in FIGS. 1 and 2). Central valve opening 9 is enclosed by an annular central chamber 20 of connecting adapter 3 (shown in FIG. 4). Annular central chamber 20 surrounds central projection 15 (shown in FIG. 4). Annular central chamber 20 is connected by a streaming flow with an outlet channel 12 (shown in FIGS. 1, 2, and 4).

Movable component 5, which can be tilted or pivoted with respect to fixed component 4, lies tightly against connecting surface 8 of fragrance container 1 while being attached to fragrance container 1, and is supported by the pressure force of springs 6 through which positional tolerances between connecting adapter 3 and fragrance container 1 are compensated.

REFERENCE SYMBOLS 1 fragrance container
2 valve plate of the valve cap of the fragrance container
3 connecting adapter
4 first (fixed) component of the connecting adapter
5 second (movable) component of the connecting adapter
6 (helical or coil) springs of the connecting adapter
7 valve cap of the fragrance container
8 connecting surface of the valve cap of the fragrance container
9 central valve opening of the valve cap
10 annular-shaped valve opening of the valve cap
11 inlet (connection or port) channel of the connecting adapter
12 outlet (connection or port channel) channel of the connecting adapter
13 intermediate space
14 neck of the fragrance container
15 central pin-shaped axially extending projection of the fixed component of the connecting adapter
16 retaining elements of the fixed component of the connecting adapter
17 hook-shaped end sections of the retaining elements
18 valve tappet of the valve plate
19 ring gap of the connecting adapter
20 annular central chamber of the connecting adapter While exemplary embodiments are described above, it is not intended that these embodiments describe all possible forms of the present invention. Rather, the words used in the specification are words of description rather than limitation, and it is understood that various changes may be made without departing from the spirit and scope of the present invention. Additionally, the features of various implementing embodiments may be combined to form further embodiments of the present invention.

What is claimed is:

1. A connecting adapter for connecting a fragrance container to a fragrance emitter device for distributing fragrance, wherein the fragrance container includes a valve tappet, the connecting adapter comprising:
a fixed component, a movable component, and a plurality of springs connected between the fixed component and the movable component, the fixed component including a central projection for engaging the valve tappet of the fragrance container and the springs being arranged symmetrically about the central projection, the movable component being pivotable with respect to the fixed component through the springs to compensate for any angular misalignment between the movable component and the fragrance container when the movable component is attached to the fragrance container.

2. The connecting adapter of claim 1 wherein:
the fixed component includes a plurality of retaining elements; and
the movable component is mounted to the fixed component through the retaining elements.

3. The connecting adapter of claim 2 wherein:
the springs are connected between the fixed component and the movable component to press the movable component against end sections of the retaining elements, respectively.

4. The connecting adapter of claim 1 wherein:
the springs individually compress differently in response to different forces applied against different locations of the movable component toward the fixed component such that the movable component is pivotable about two directional axes in a plane.

5. A fragrance apparatus for distributing fragrance in a vehicle, the fragrance apparatus comprising:
a fragrance container; and
a connecting adapter having a fixed component, a movable component, and a plurality of springs connected between the fixed component and the movable component, the connecting adapter being connected to the fragrance container with the movable component being arranged against the fragrance container, the movable component being pivotable with respect to the fixed component through the springs to compensate for any angular misalignment between the connecting adapter and the fragrance container.

6. The fragrance apparatus of claim 5 wherein:
the fixed component is attachable to a fragrance emitter device; and
the fragrance container is connected to the fragrance emitter device through the connecting adapter when the fixed component is attached to the fragrance emitter device.

7. The fragrance apparatus of claim 5 wherein:
the fixed component includes a plurality of retaining elements; and
the movable component is mounted to the fixed component through the retaining elements.

8. The fragrance apparatus of claim 7 wherein:
the springs are connected between the fixed component and the movable component to press the movable component against end sections of the retaining elements, respectively.

9. The fragrance apparatus of claim 5 wherein:
the springs individually compress differently in response to different forces applied against different locations of the movable component toward the fixed component such that the movable component is pivotable about two directional axes in a plane.

10. The fragrance apparatus of claim 5 wherein:
the fragrance container includes a valve cap having a valve tappet and a spring-loaded valve plate; and
the fixed component includes a central projection for engaging the valve tappet to open the valve plate while the connecting adapter is connected to the fragrance container.

11. The fragrance apparatus of claim 10 wherein:
the springs are arranged symmetrically about the central projection.

12. A fragrance apparatus for distributing fragrance in a vehicle, the fragrance apparatus comprising:
a fragrance container having a valve cap including a connecting surface; and
a connecting adapter having a fixed component, a movable component, and a plurality of springs connected between the fixed component and the movable component, the movable component being attached to the connecting surface of the valve cap of the fragrance container to connect the connecting adapter to the fragrance container, the movable component being pivotable with respect to the fixed component through the springs to compensate for any angular misalignment between the movable component and the connecting surface of the valve cap of the fragrance container.

13. The fragrance apparatus of claim 12 wherein:
the fixed component includes a plurality of retaining elements; and
the movable component is mounted to the fixed component through the retaining elements.

14. The fragrance apparatus of claim 13 wherein:
the springs are connected between the fixed component and the movable component to press the movable component against end sections of the retaining elements, respectively.

15. The fragrance apparatus of claim 12 wherein:
the springs individually compress differently in response to different forces applied against different locations of the movable component toward the fixed component such that the movable component is pivotable about two directional axes in a plane.

16. The fragrance apparatus of claim 12 wherein:
the valve cap of the fragrance container has a spring-loaded valve plate including a valve tappet; and
the fixed component includes a central projection for engaging the valve tappet to open the valve plate while the movable component is attached to the connecting surface of the valve cap of the fragrance container.

17. The fragrance apparatus of claim 16 wherein:
the springs are arranged symmetrically about the central projection.

18. The fragrance apparatus of claim 16 wherein:
the valve plate of the valve cap of the fragrance container further includes at least one valve opening, the at least one valve opening being exposed when the valve plate is opened.

19. The fragrance apparatus of claim 18 wherein:
the movable component includes a chamber which is in fluid communication with one of the at least one valve opening when the valve plate is opened while the movable component is attached to the connecting surface of the valve cap of the fragrance container.

* * * * *